US011124770B2

(12) United States Patent
Iseoka et al.

(10) Patent No.: US 11,124,770 B2
(45) Date of Patent: Sep. 21, 2021

(54) MYOCARDIAL CELL SHEET (71) Applicants: TERUMO KABUSHIKI KAISHA, Tokyo (JP); OSAKA UNIVERSITY, Suita (JP)

(72) Inventors: Hiroko Iseoka, Kanagawa (JP); Yoshiki Sawa, Suita (JP); Shigeru Miyagawa, Suita (JP); Satsuki Fukushima, Suita (JP)

(73) Assignees: TERUMO KABUSHIKI KAISHA, Tokyo (JP); OSAKA UNIVERSITY, Suita (JP)

( * ) Notice: Subject to any disclaimer, the term of this patent is extended or adjusted under 35 U.S.C. 154(b) by 0 days.

(21) Appl. No.: 15/594,011

(22) Filed: May 12, 2017

(65) Prior Publication Data
US 2017/0247658 A1    Aug. 31, 2017

Related U.S. Application Data (63) Continuation of application No. PCT/JP2015/081777, filed on Nov. 11, 2015.

(30) Foreign Application Priority Data

Nov. 12, 2014 (JP) .............................. JP2014-230100

(51) Int. Cl.
C12N 5/077 (2010.01)
A61K 35/34 (2015.01)
A61K 35/12 (2015.01)

(52) U.S. Cl.
CPC ............ *C12N 5/0657* (2013.01); *A61K 35/12* (2013.01); *A61K 35/34* (2013.01); *C12N 2501/115* (2013.01); *C12N 2501/155* (2013.01); *C12N 2501/16* (2013.01); *C12N 2501/165* (2013.01); *C12N 2501/415* (2013.01); *C12N 2501/999* (2013.01); *C12N 2506/45* (2013.01)

(58) Field of Classification Search
None
See application file for complete search history.

(56) References Cited

U.S. PATENT DOCUMENTS

| 9,764,063 | B2* | 9/2017 | Yamashita | ............. A61K 35/34 |
| 2007/0092492 | A1 | 4/2007 | Matsuda et al. | |
| 2014/0056859 | A1* | 2/2014 | Okano | ..................... A61K 9/70 |
| | | | | 424/93.7 |
| 2015/0297794 | A1 | 10/2015 | Yamashita et al. | |

FOREIGN PATENT DOCUMENTS

| EP | 2 692 859 A1 | 2/2014 | |
| JP | 2007-528755 A | 10/2007 | |
| WO | WO 12/133945 | * 10/2012 | ............. C12N 5/071 |
| WO | 2013/084009 A1 | 6/2013 | |
| WO | 2014/014119 A1 | 1/2014 | |
| WO | WO 2013/137491 | 8/2015 | |

OTHER PUBLICATIONS

Stratman et al, Development, 2017, vol. 144, pp. 115-127. (Year: 2017).*
NCBI Gene "PECAM1" information listing. Accessed Mar. 29, 2019. (Year: 2019).*
NCBI Gene PACTA2 information listing. Accessed Mar. 29, 2019 (Year: 2019).*
Ja et al, Journal Cellular Molecular Medicine, 2016, vol. 20, No. 2, pp. 323-332. (Year: 2016).*
Myers et al, Arteriosclerosis and Thrombosis Vascular Biology, 1998, vol. 18, pp. 717-722. (Year: 1998).*
Machine Translation of WO 13/0137491 to Yamashita et al (Year: 2013).*
Okita et al, Nature, 2007, vol. 448, pp. 313-317. (Year: 2007).*
Notification of Transmittal of Translation of the International Preliminary Report on Patentability (Forms PCT/IB/338 and PCT/IB/373) and the Written Opinion of the International Searching Authority (Form PCT/ISA/237) dated May 16, 2017. (9 pgs).
Shimizu, T., et al. "Fabrication of Pulsatile Cardiac Tissue Grafts using a Novel 3-Dimensional Cell Sheet Manipulation Technique and Temperature-Responsive Cell Culture Surfaces", Circulation Research, vol. 90, Issue 3, e40-e48, Jan. 24, 2002.
Matsuura, K. et al. "Creation of Mouse Embryonic Stem Cell-Derived Cardiac Cell Sheets", Biomaterials, vol. 32, Issue 30, pp. 7355-7362, Oct. 31, 2011.
Kawamura, M. et al. "Feasibility, Safety, and Therapeutic Efficacy of Human Induced Pluripotent Stem Cell-Derived Cardiomyocyte Sheets in a Porcine Ischemic Cardiomyopathy Model", Circulation vol. 126, Issue 11 suppl 1, pp. S29-S37, Sep. 2012.
Taura, D. et al. "Induction and Isolation of Vascular Cells from Human Induced Pluripotent Stem Cells—brief report", Arteriosclerosis, Thrombosis, and Vascular Biology, vol. 29, Issue 7, pp. 1100-1103, Jul. 2009.
Dubois et al., "SIRPA is a Specific Cell-Surface Marker for Isolating Cardiomyocytes Derived from Human Pluripotent Stem Cells," Nature Biotechnology, (Nov. 2011), vol. 29, No. 11, pp. 1011-1018.

(Continued)

*Primary Examiner* — Allison M Fox
(74) *Attorney, Agent, or Firm* — Buchanan Ingersoll & Rooney PC (57) ABSTRACT A sheet-shaped cell culture is disclosed that includes myocardial cells derived from pluripotent stem cells and has excellent functional properties. A sheet-shaped cell culture obtained by culturing a cell population that includes myocardial cells derived from pluripotent stem cells, wherein the proportion of the number of the myocardial cells derived from pluripotent stem cells to the total number of cells in the cell population is 50% to 70%; a method of producing the sheet-shaped cell culture; a composition including the sheet-shaped cell culture; and a method of treating a disease using the sheet-shaped cell culture or the composition.

4 Claims, 1 Drawing Sheet

(56) References Cited

OTHER PUBLICATIONS

Iseoka et al., "Development of Functional Tissue-Engineered Artificial Cardiac Construct using Human Induced Pluripotent Stem Cells; Optimizing the Cell Components to Mimic Cardiac Tissue," AHA ePosters, Scientific Sessions, (Nov. 15-19, 2014), (4 pages).
Iseoka et al., "Study on the Purity of Myocardial Cells Optimal for the Myocardial Cell Sheet Derived from iPS Cells," Regenerative Medicine, (Feb. 1, 2015), vol. 14, pp. 354, with English Translation, (5 pages).
Iseoka et al., "Pivotal Role of Non-Cardiomyocytes in Electromechanical and Therapeutic Potential of Induced Pluripotent Stem Cell-Derived Engineered Cardiac Tissue," Tissue Engineering & Regenerative Medicine International Society: Part A, (2018), vol. 24, No. 3 and 4, pp. 287-300.
Masumoto et al., "Pluripotent Stem Cell-Engineered Cell Sheets Reassembled with Defined Cardiovascular Populations Ameliorate Reduction in Infarct Heart Function Through Cardiomyocyte-Mediated Neovascularization," Stem Cells, (Jun. 2012), vol. 30, No. 6, pp. 1196-1205.
Masumoto, "Pluripotent Stem Cell-Derived Defined Cardiac Tissue Sheets Demonstrate Cardiac Repair Through Cardiomyocyte-Mediated Neovascularization," Journal of the Japanese Society for Regenerative Medicine, (Nov. 2012), vol. 11, No. 4, pp. 372-378, with English Translation, (30 pages).
Masumoto et al., "Human iPS Cell-Engineered Cardiac Tissue Sheets with Cardiomyocytes and Vascular Cells for Cardiac Regeneration," Scientific Reports, (Oct. 22, 2014), vol. 4, No. 1, pp. 1-7.
Matsuura et al., "Fabrication of Mouse Embryonic Stem Cell-Derived Layered Cardiac Cell Sheets Using a Bioreactor Culture System," PLoS One, (Dec. 20, 2012) vol. 7, No. 12, e52176, pp. 1-11.
Matsuura et al., "Creation of Human Cardiac Cell Sheets using Pluripotent Stem Cells," Biochemical and Biophysical Research Communications, (Aug. 24, 2012), vol. 425, Issue 2, pp. 321-327.
Thavandiran et al., "Design and Formulation of Functional Pluripotent Stem Cell-Derived Cardiac Microtissues," PNAS, (Nov. 18, 2013), vol. 110,. No. 49, pp. E4698-E4707.
The extended European Search Report dated Jun. 15, 2018, by the European Patent Office in corresponding European Patent Application No. 15858532.3-1112. (9 pages).
Miki et al., "Bioengineered Myocardium Derived from Induced Pluripotent Stem Cells Improves Cardiac Function and Attenuates Cardiac Remodeling Following Chronic Myocardial Infarction in Rats," Stem Cells Translational Medicine, (May 2012), vol. 1, No. 5, pp. 430-437.
Claassen et al., "ROCK Inhibition Enhances the Recovery and Growth of Cryopreserved Human Embryonic Stem Cells and Human Induced Pluripotent Stem Cells", Mol Reprod Dev. Aug. 2009; 76(8): 722-732.
International Search Report (PCT/ISA/210) dated Feb. 9, 2016, by the Japanese Patent Office as the International Searching Authority for International Application No. PCT/JP2015/081777.
Written Opinion (PCT/ISA/237) dated Feb. 9, 2016, by the Japanese Patent Office as the International Searching Authority for International Application No. PCT/JP2015/081777.

\* cited by examiner

MYOCARDIAL CELL SHEET

CROSS-REFERENCES TO RELATED APPLICATIONS

This application is a continuation of International Application No. PCT/JP2015/081777 filed on Nov. 11, 2015, which claims priority to Japanese Application No. 2014-230100, filed on Nov. 11, 2014, the entire contents of which are incorporated herein by reference.

TECHNICAL FIELD

The present disclosure relates to a sheet-shaped cell culture including myocardial cells derived from pluripotent stem cells, a method of producing the same, a composition, including the sheet-shaped cell culture, and a method of treating a disease using the sheet-shaped cell culture.

BACKGROUND DISCUSSION

Myocardial cells of adults are poor in self-replication ability, and in the case where a myocardial tissue is injured, it is extremely difficult to repair the injured tissue. In recent years, for repairing an injured myocardial tissue, attempts have been made to transplant a graft including myocardial cells produced by a cell engineering technique to the affected area (JP-A-2007-528755, and Shimizu et al., Circ Res. 2002 Feb. 22; 90(3): e40-e48). As a supply source of myocardial cells for use in the production of such a graft, myocardial cells derived from pluripotent stem cells such as embryonic stem cells (ES cells) and induced pluripotent stem cells (iPS cells) have recently been drawing attention, and production of sheet-shaped cell cultures including such myocardial cells derived from pluripotent stem cells and therapeutic experiments thereof using animals have been attempted (Matsuura et al., Biomaterials. 2011 October; 32(30): 7355-62, and Kawamura et al., Circulation. 2012 Sep. 11; 126(11 Suppl 1): S29-37). However, the development of sheet-shaped cell cultures including myocardial cells derived from pluripotent stem cells has just been started, and there are still unclear points in regard of functional properties thereof, and factors having influences thereon.

SUMMARY

A sheet-shaped cell culture is disclosed that includes myocardial cells derived from pluripotent stem cells and has useful functional properties, a method of producing the same, a graft including the sheet-shaped cell culture, and a method of treating a disease using the sheet-shaped cell culture.

In accordance with an exemplary embodiment, the present inventors found that when the proportion of the number of myocardial cells derived from pluripotent stem cells to the total number of cells in a cell population for use in forming a sheet-shaped cell culture is controlled to within the range of 50% to 70%, the ability to produce a cytokine useful for treatment of a disease is thereby enhanced.

Specifically, the present invention relates to the following.

A sheet-shaped cell culture is disclosed, which is obtained by culturing a cell population that includes myocardial cells derived from pluripotent stem cells, wherein the proportion of the number of the myocardial cells derived from pluripotent stem cells to the total number of cells in the cell population is 50% to 70%.

The sheet-shaped cell culture, wherein the cell population further includes cells selected from the group consisting of αSMA positive cells, CD31 positive cells, and TE-7 antigen positive cells.

The sheet-shaped cell culture being higher in cytokine producing ability than a sheet-shaped cell culture obtained by culturing a cell population wherein the proportion of the number of myocardial cells derived from pluripotent stem cells to the total number of cells in the cell population is not more than 25% or not less than 90%.

A method is disclosed of producing the sheet-shaped cell culture, the method including: (1) a step of subjecting pluripotent stem cells to a myocardial cell derivation treatment to obtain a first cell population including myocardial cells; (2) a step of obtaining a second cell population including the myocardial cells derived from the first cell population obtained in the step (1); and (3) a step of culturing the second cell population obtained in the step (2) to form a sheet-shaped cell culture, wherein the proportion of the number of the myocardial cells to the total number of cells in the second cell population is 50% to 70%.

A composition is disclosed including the sheet-shaped cell culture as disclosed herein.

The composition as disclosed herein for treating a heart disease.

A method of treating a disease in a subject, the method including applying an effective amount of the sheet-shaped cell culture according to the sheet-shaped cell culture or the composition disclosed herein to the subject in need thereof.

A method is disclosed of enhancing a cytokine producing ability of a sheet-shaped cell culture including myocardial cells derived from pluripotent stem cells, the method including: (1) a step of subjecting pluripotent stem cells to a myocardial cell derivation treatment to obtain a first cell population including myocardial cells; (2) a step of obtaining a second cell population including the myocardial cells derived from the first cell population obtained in the step (1); and (3) a step of culturing the second cell population obtained in the step (2) to form a sheet-shaped cell culture, wherein the proportion of the number of the myocardial cells to the total number of cells in the second cell population is 50% to 70%.

In accordance with an exemplary embodiment, the sheet-shaped cell culture of the present disclosure has a high ability to produce a cytokine useful for treatment of a disease, and can give an excellent therapeutic effect, so that a huge contribution thereof to the medical field can be expected.

DETAILED DESCRIPTION

Unless defined otherwise herein, all the technical terms and scientific terms used herein have the same meanings as usually understood by those skilled in the art. All the patents, applications and other publications (inclusive of information available from the Internet) referred to herein are cited herein by reference in their entirety.

An aspect of the present disclosure relates to a sheet-shaped cell culture obtained by culturing a cell population that includes myocardial cells derived from pluripotent stem cells, wherein the proportion of the number of the myocardial cells derived from pluripotent stem cells to the total number of cells in the cell population is more than approximately 25% and less than approximately 90%, preferably approximately 30% to approximately 80%, more preferably approximately 40% to approximately 75%, and particularly preferably approximately 50% to approximately 70% (the sheet-shaped cell culture may hereinafter be referred to as "the sheet-shaped cell culture of the present disclosure").

The pluripotent stem cell is a term known in this technical field, and means a cell having an ability to differentiate into various tissues in a living body. Non-limitative examples of the pluripotent stem cells include embryonic stem cells (ES cells), nuclear transplantation embryonic stem cells (ntES cells), and induced pluripotent stem cells (iPS cells).

In the present disclosure, the "myocardial cells derived from pluripotent stem cells" means cells having characteristic features of myocardial cells derived from pluripotent stem cells. Examples of the characteristic features of the myocardial cells include, but are not limited to, the expression of a myocardial cell marker and the presence of autonomous beating. Non-limitative examples of the myocardial cell marker include cardiac troponin T (c-TNT), CD172a (also known as SIRPA or SHPS-1), KDR (also known as CD309, FLK1 or VEGFR2), PDGFRA, EMILIN2, and VCAM. In accordance with an exemplary embodiment, the myocardial cells derived from pluripotent stem cells are c-TNT positive and/or CD172a positive. The myocardial cells can be obtained by deriving myocardial cells from pluripotent stem cells, namely, subjecting pluripotent stem cells to a myocardial cell derivation treatment. A variety of techniques for deriving myocardial cells from pluripotent stem cells are known (for example, Burridge et al., Cell Stem Cell. 2012 Jan. 6; 10(1): 16-28). Non-limitative examples of such a derivation method include a method by formation of embryoid body, a method by monolayer differentiation culture, and a method by compelled coagulation. In any of the methods, the derivation efficiency can be enhanced by sequentially reacting with a mesoderm inducing factor (for example, activin A, BMP4, bFGF, VEGF, SCF), a cardiac specification factor (for example, VEGF, DKK1, Wnt signal inhibitor (for example, IWR-1, IWP-2, IWP-4), a BMP signal inhibitor (for example, NOGGIN), a TGFβ/activin/NODAL signal inhibitor (for example, SB431542), a retinoic acid signal inhibitor), and a cardiac differentiation factor (for example, VEGF, bFGF, DKK1). In an exemplary embodiment, the treatment for deriving myocardial cells from pluripotent stem cells includes sequentially bringing an embryoid body formed under suspension culture to reaction with (1) BMP4, (2) a combination of BMP4, bFGF and activin A, (3) IWR-1, and (4) a combination of VEGF and bFGF.

The myocardial cells derived from pluripotent stem cells can be enhanced in purity by purification after derivation. Examples of purifying methods include various separating methods using a marker specific to myocardial cells (for example, cell surface marker), for example, magnetic cell separation method (MACS), flow cytometry method, affinity separation method, a method of causing expression of a selection marker (for example, antibiotic-resistant gene) by a specific promotor, and, further, a method by a combination of these methods (see, for example, the above-mentioned Burridge et al.). Examples of the cell surface marker specific to myocardial cells include CD172a, KDR, PDGFRA, EMILIN2, and VCAM. In addition, examples of the promotor specific to myocardial cells include NKX2-5, MYH6, MLC2V, and ISL1. In an exemplary embodiment, the myocardial cells are purified based on CD172a, which is a cell surface marker.

The myocardial cells derived from pluripotent stem cells may be a myocardial cell population obtained by deriving myocardial cells from pluripotent stem cells in the aforesaid manner and optionally subjecting the myocardial cells to the aforesaid purification treatment. The purity of the myocardial cells in the myocardial cell population (for example, the proportion of the number of myocardial cell marker positive cells to the total number of cells in the myocardial cell population) may, for example, be more than approximately 85%, more than approximately 86%, more than approximately 87%, more than approximately 88%, more than approximately 89%, more than approximately 90%, more than approximately 91%, more than approximately 92%, more than approximately 93%, more than approximately 94%, more than approximately 95%, more than approximately 96%, more than approximately 97%, more than approximately 98%, or more than approximately 99%. In an exemplary embodiment, the myocardial cells derived from pluripotent stem cells in the present disclosure are a myocardial cell population wherein the purity of the myocardial cells is more than 90%.

As the cell population including the myocardial cells derived from pluripotent stem cells, a cell population obtained after deriving myocardial cells by subjecting pluripotent stem cells to a myocardial cell derivation treatment may be utilized as it is, or a cell population enhanced in purity by purification of myocardial cells from a cell population after derivation of myocardial cells may be utilized, or a cell population lowered in purity by removing part of myocardial cells from a cell population after derivation of myocardial cells may be utilized, or a mixture obtained by mixing a purified myocardial cell population with other cell population may be utilized. In an exemplary embodiment, the cell population including the myocardial cells derived from pluripotent stem cells is obtained by mixing a myocardial cell population obtained by purification of a cell population obtained by subjecting pluripotent stem cells to a myocardial cell derivation treatment with a non-myocardial cell population remaining after the purification, in a predetermined ratio.

In the present disclosure, the "sheet-shaped cell culture" refers to a sheet-shaped body wherein cells are interconnected. The cells may be interconnected directly (inclusive of the case of interconnection through cell elements such as adhesion molecules) and/or through an intervening substance. The intervening substance is not particularly limited so long as it is a substance capable of at least physically (mechanically) interconnecting the cells, and examples thereof include, but are not limited to, an extracellular matrix. The intervening substance is preferably one derived from cells, particularly one that is derived from the cells constituting the cell culture. The cells are interconnected at least physically (mechanically), and may be further interconnected functionally, for example, chemically or electrically. The sheet-shaped cell culture may be one that includes one cell layer (monolayer), or may be one that includes two or more cell layers (laminated (multilayer), for example, two layers, three layers, four layers, five layers, or six layers).

In accordance with an exemplary embodiment, the sheet-shaped cell culture preferably does not include a scaffold (support). A scaffold may be used in this technical field by adhering cells onto its surface and/or to its inside for the purpose of maintaining the physical integrity of the sheet-shaped cell culture, and known examples of the scaffold include a membrane made of polyvinylidene difluoride (PVDF). The sheet-shaped cell culture in the present disclosure may be one that can at least maintain its physical integrity without such a scaffold. In addition, preferably, the sheet-shaped cell culture includes a substance or substances derived from the cells constituting the cell culture, and does not include other substances.

In an exemplary embodiment, the cell population including the myocardial cells derived from pluripotent stem cells further include one or more kinds of non-myocardial cells selected from the group consisting of αSMA positive cells, CD31 positive cells, and TE-7 antigen positive cells. The αSMA and CD31 are known proteins, and TE-7 antigen is an antigen identified by TE-7 antibody (clone TE-7, mouse IgG1, made by Merck Millipore Corporation) (see, for example, Goodpaster et al., J Histochem Cytochem. 2008 April; 56(4): 347-58). Non-limitative examples of αSMA positive cells include smooth muscle cells and myofibroblasts; non-limitative examples of CD31 positive cells include vascular endothelial cells; non-limitative examples of TE-7 antigen positive cells include fibroblasts and myofibroblasts. The non-myocardial cells can be identified by use of, for example, an antibody binding specifically to αSMA, CD31 or TE-7. The non-myocardial cells may be isolated from a living body by a known method, or may be derived from pluripotent stem cells or the like.

In an exemplary embodiment, the cell population including the myocardial cells derived from pluripotent stem cells includes αSMA positive cells, CD31 positive cells, and TE-7 antigen positive cells, in addition to the myocardial cells. In an embodiment, the αSMA positive cells, CD31 positive cells, and TE-7 antigen positive cells are obtained by subjecting pluripotent stem cells to a myocardial cell derivation treatment. In a preferred embodiment, the αSMA positive cells, CD31 positive cells, and TE-7 antigen positive cells are included in a non-myocardial cell population obtained by removing myocardial cells from a cell population obtained by subjecting pluripotent stem cells to a myocardial cell derivation treatment. The removal of myocardial cells can be achieved by, for example, purification of the above-mentioned myocardial cells.

The proportion of the number of the αSMA positive cells to the total number of cells in the non-myocardial cell population may, for example, be approximately 65% to approximately 95%, approximately 75% to approximately 93%, approximately 80% to approximately 91%, approximately 85% to approximately 90%, or approximately 86% to approximately 89%; the proportion of the number of the CD31 positive cells to the total number of cells in the non-myocardial cell population may, for example, be approximately 1% to approximately 10%, approximately 2% to approximately 9%, approximately 3% to approximately 8%, approximately 3.5% to approximately 7%, or approximately 4% to approximately 6%; and the proportion of the number of the TE-7 antigen positive cells to the total number of cells in the non-myocardial cell population may, for example, be approximately 0.1% to approximately 50%, approximately 0.2% to approximately 45%, approximately 0.4% to approximately 40%, approximately 0.5% to approximately 35%, or approximately 0.6% to approximately 32%.

In an exemplary embodiment, the proportion of the number of the TE-7 antigen positive cells to the total number of cells in the non-myocardial cell population may, for example, be approximately 0.1% to approximately 10%, approximately 0.2% to approximately 5%, approximately 0.4% to approximately 2%, approximately 0.5% to approximately 1%, or approximately 0.6% to approximately 0.7%. In another exemplary embodiment, the proportion of the number of the TE-7 antigen positive cells to the total number of cells in the non-myocardial cell population may, for example, be approximately 0.5% to approximately 50%, approximately 3% to approximately 45%, approximately 7.5% to approximately 40%, approximately 15% to approximately 35%, or approximately 30% to approximately 32%. In another exemplary embodiment, the proportion of the number of the TE-7 antigen positive cells to the total number of cells in the non-myocardial cell population may, for example, be approximately 0.2% to approximately 40%, approximately 0.5% to approximately 32%, approximately 3% to approximately 25%, approximately 7.5% to approximately 20%, or approximately 15% to approximately 17%.

Note that since cells positive for two or more kinds of markers selected from αSMA, CD31 and TE-7 antigen can be present in the non-myocardial cell population (for example, myofibroblasts are considered to be positive for both αSMA and TE-7 antigen (see, for example, the above-mentioned Goodpaster et al.)), the sum total of the percentages of the numbers of non-myocardial cell marker positive cells to the total number of cells in the non-myocardial cell population may exceed 100%.

The proportion of the number of the αSMA positive cells to the total number of cells in the cell population including the myocardial cells derived from pluripotent stem cells may, for example, be approximately 6.5% to approximately 71.25%, approximately 7.5% to approximately 69.75%, approximately 8% to approximately 68.25%, approximately 8.5% to approximately 67.5%, or approximately 8.6% to approximately 66% in the case where the proportion of the number of the myocardial cells to the total number of cells in the cell population is more than approximately 25% and less than approximately 90%, may, for example, be approximately 13% to approximately 66.5%, approximately 15% to approximately 65.1%, approximately 16% to approximately 63.7%, approximately 17% to approximately 63%, or approximately 17.2% to approximately 62.3% in the case where the proportion of the number of the myocardial cells is approximately 30% to approximately 80%, may be approximately 16.25% to approximately 57%, approximately 18.75% to approximately 55.8%, approximately 20% to approximately 54.6%, approximately 21.25% to approximately 54%, or approximately 21.5% to approximately 53.4% in the case where the proportion of the number of the myocardial cells is approximately 40% to approximately 75%, and may, for example, be approximately 19.5% to approximately 47.5%, approximately 22.5% to approximately 46.5%, approximately 24% to approximately 45.5%, approximately 25.5% to approximately 45%, or approximately 25.8% to approximately 44.5% in the case where the proportion of the number of the myocardial cells is approximately 50% to approximately 70%.

The proportion of the number of the CD31 positive cells to the total number of cells in the cell population including the myocardial cells derived from pluripotent stem cells may, for example, be approximately 0.1% to approximately 7.5%, approximately 0.2% to approximately 6.75%, approximately 0.3% to approximately 6%, approximately 0.35% to approximately 5.25%, or approximately 0.4% to approximately 4.5% in the case where the proportion of the number of myocardial cells to the total number of cells in the cell population is more than approximately 25% and less than approximately 90%, may, for example, be approximately 0.2% to approximately 7%, approximately 0.4% to approximately 6.3%, approximately 0.6% to approximately 5.6%, approximately 0.7% to approximately 4.9%, or approximately 0.8% to approximately 4.2% in the case where the proportion of the number of the myocardial cells is approximately 30% to approximately 80%, may, for example, be approximately 0.25% to approximately 6%, approximately 0.5% to approximately 5.4%, approximately 0.75% to approximately 4.8%, approximately 0.88% to approximately 4.2%, or approximately 1% to approximately 3.6% in the case where the proportion of the number of the myocardial cells is approximately 40% to approximately 75%, and may, for example, be approximately 0.3% to approximately 5%, approximately 0.6% to approximately 4.5%, approximately 0.9% to approximately 4%, approximately 1.05% to approximately 3.5%, or approximately 1.2% to approximately 3% in the case where the proportion of the number of the myocardial cells is approximately 50% to approximately 70%.

The proportion of the number of the TE-7 antigen positive cells to the total number of cells in the cell population including the myocardial cells derived from pluripotent stem cells may, for example, be approximately 0.01% to approximately 37.5%, approximately 0.02% to approximately 33.75%, approximately 0.04% to approximately 30%, approximately 0.05% to approximately 26.25%, or approximately 0.06% to approximately 24% in the case where the proportion of the number of the myocardial cells to the total number of cells in the cell population is more than approximately 25% and less than approximately 90%, may, for example, be approximately 0.02% to approximately 35%, approximately 0.04% to approximately 31.5%, approximately 0.08% to approximately 28%, approximately 0.1% to approximately 24.5%, or approximately 0.12% to approximately 22.4% in the case where the proportion of the number of the myocardial cells is approximately 30% to approximately 80%, may, for example, be approximately 0.03% to approximately 30%, approximately 0.05% to approximately 27%, approximately 0.1% to approximately 24%, approximately 0.13% to approximately 21%, or approximately 0.15% to approximately 19.2% in the case where the proportion of the number of the myocardial cells is approximately 40% to approximately 75%, and may, for example, be approximately 0.03% to approximately 25%, approximately 0.06% to approximately 22.5%, approximately 0.12% to approximately 20%, approximately 0.15% to approximately 17.5%, or approximately 0.18% to approximately 16% in the case where the proportion of the number of the myocardial cells is approximately 50% to approximately 70%.

In an exemplary embodiment, the proportion of the number of the TE-7 antigen positive cells to the total number of cells in the cell population including the myocardial cells derived from pluripotent stem cells may, for example, be approximately 0.01% to approximately 7.5%, approximately 0.02% to approximately 3.75%, approximately 0.04% to approximately 1.5%, approximately 0.05% to approximately 0.75%, or approximately 0.06% to approximately 0.53% in the case where the proportion of the number of the myocardial cells to the total number of cells in the cell population is more than approximately 25% and less than approximately 90%, may, for example, be approximately 0.02% to approximately 7%, approximately 0.04% to approximately 3.5%, approximately 0.08% to approximately 1.4%, approximately 0.1% to approximately 0.7%, or approximately 0.12% to approximately 0.49% in the case where the proportion of the number of the myocardial cells is approximately 30% to approximately 80%, may, for example, be approximately 0.03% to approximately 6%, approximately 0.05% to approximately 3%, approximately 0.1% to approximately 1.2%, approximately 0.13% to approximately 0.6%, or approximately 0.15% to approximately 0.42% in the case where the proportion of the number of the myocardial cells is approximately 40% to approximately 75%, and may, for example, be approximately 0.03% to approximately 5%, approximately 0.06% to approximately 2.5%, approximately 0.12% to approximately 1%, approximately 0.15% to approximately 0.5%, or approximately 0.18% to approximately 0.35% in the case where the proportion of the number of the myocardial cells is approximately 50% to approximately 70%.

In another exemplary embodiment, the proportion of the number of the TE-7 antigen positive cells to the total number of cells in the cell population including the myocardial cells derived from pluripotent stem cells may, for example, be approximately 0.05% to approximately 37.5%, approximately 0.3% to approximately 33.75%, approximately 0.75% to approximately 30%, approximately 1.5% to approximately 26.25%, or approximately 3% to approximately 24% in the case where the proportion of the number of the myocardial cells to the total number of cells in the cell population is more than approximately 25% and less than approximately 90%, may, for example, be approximately 0.1% to approximately 35%, approximately 0.6% to approximately 31.5%, approximately 1.5% to approximately 28%, approximately 3% to approximately 24.5%, or approximately 6% to approximately 22.4% in the case where the proportion of the number of the myocardial cells is approximately 30% to approximately 80%, may, for example, be approximately 0.13% to approximately 30%, approximately 0.75% to approximately 27%, approximately 1.88% to approximately 24%, approximately 3.75% to approximately 21%, or approximately 7.5% to approximately 19.2% in the case where the proportion of the number of the myocardial cells is approximately 40% to approximately 75%, and may, for example, be approximately 0.15% to approximately 25%, approximately 0.9% to approximately 22.5%, approximately 2.25% to approximately 20%, approximately 4.5% to approximately 17.5%, or approximately 9% to approximately 16% in the case where the proportion of the number of the myocardial cells is approximately 50% to approximately 70%.

In another exemplary embodiment, the proportion of the number of the TE-7 antigen positive cells to the total number of cells in the cell population including the myocardial cells derived from pluripotent stem cells may, for example, be approximately 0.02% to approximately 30%, approximately 0.05% to approximately 24%, approximately 0.3% to approximately 18.75%, approximately 0.75% to approximately 15%, or approximately 1.5% to approximately 12.75% in the case where the proportion of the number of the myocardial cells to the total number of cells in the cell population is more than approximately 25% and less than approximately 90%, may, for example, be approximately 0.04% to approximately 28%, approximately 0.1% to approximately 22.4%, approximately 0.6% to approximately 17.5%, approximately 1.5% to approximately 14%, or approximately 3% to approximately 11.9% in the case where the proportion of the number of the myocardial cells is approximately 30% to approximately 80%, may, for example, be approximately 0.05% to approximately 24%, approximately 0.13% to approximately 19.2%, approximately 0.75% to approximately 15%, approximately 1.88% to approximately 12%, or approximately 3.75% to approximately 10.2% in the case where the proportion of the number of the myocardial cells is approximately 40% to approximately 75%, and may, for example, be approximately 0.06% to approximately 20%, approximately 0.15% to approximately 16%, approximately 0.9% to approximately 12.5%, approximately 2.25% to approximately 10%, or approximately 4.5% to approximately 8.5% in the case where the proportion of the number of the myocardial cells is approximately 50% to approximately 70%.

Note that since cells that are positive for two or more kinds of markers selected from αSMA, CD31 and TE-7 antigen can be present in the cell population including the myocardial cells derived from pluripotent stem cells, the sum total of the percentages of the numbers of marker positive cells to the total number of cells in the cell population may exceed 100%. In addition, in the case where the cell population including the myocardial cells derived from pluripotent stem cells is a mixture obtained by mixing the myocardial cells derived from pluripotent stem cells with the above-mentioned non-myocardial cell population, the proportion of the number of each kind of non-myocardial cell marker positive cells to the total number of cells in the cell population including the myocardial cells derived from pluripotent stem cells can be calculated by multiplying the proportion of the number of each kind of non-myocardial cell marker positive cells to the total number of cells in aforesaid non-myocardial cell population and the proportion of the total number of cells in the non-myocardial cell population to the total number of cells in the cell population including the myocardial cells derived from pluripotent stem cells.

In the above-mentioned non-myocardial cell population or the cell population including the myocardial cells derived from pluripotent stem cells, the ratio between the number of αSMA positive cells and the number of CD31 positive cells may, for example, be (approximately 65 to approximately 95):(approximately 1 to approximately 10), (approximately 75 to approximately 93):(approximately 2 to approximately 9), (approximately 80 to approximately 91):(approximately 3 to approximately 8), (approximately 85 to approximately 90):(approximately 3.5 to approximately 7), or (approximately 86 to approximately 89):(approximately 4 to approximately 6); the ratio between the number of αSMA positive cells and the number of TE-7 antigen positive cells may, for example, be (approximately 65 to approximately 95):(approximately 0.1 to approximately 50), (approximately 75 to approximately 93):(approximately 0.2 to approximately 45), (approximately 80 to approximately 91):(approximately 0.4 to approximately 40), (approximately 85 to approximately 90):(approximately 0.5 to approximately 35), or (approximately 86 to approximately 89):(approximately 0.6 to approximately 32); the ratio between the number of CD31 positive cells and the number of TE-7 antigen positive cells may, for example, be (approximately 1 to approximately 10):(approximately 0.1 to approximately 50), (approximately 2 to approximately 9): (approximately 0.2 to approximately 45), (approximately 3 to approximately 8):(approximately 0.4 to approximately 40), (approximately 3.5 to approximately 7):(approximately 0.5 to approximately 35), or (approximately 4 to approximately 6):(approximately 0.6 to approximately 32); and the ratio between αSMA positive cells and the number of CD31 positive cells and the number of TE-7 antigen positive cells may, for example, be (approximately 65 to approximately 95):(approximately 1 to approximately 10):(approximately 0.1 to approximately 50), (approximately 75 to approximately 93):(approximately 2 to approximately 9):(approximately 0.2 to approximately 45), (approximately 80 to approximately 91):(approximately 3 to approximately 8): (approximately 0.4 to approximately 40), (approximately 85 to approximately 90):(approximately 3.5 to approximately 7):(approximately 0.5 to approximately 35), or (approximately 86 to approximately 89):(approximately 4 to approximately 6):(approximately 0.6 to approximately 32).

In accordance with an exemplary embodiment, the cells constituting the sheet-shaped cell culture can be derived from any organism that can be treated by the sheet-shaped cell culture. Examples of such an organism include, but are not limited to, humans, nonhuman primates, dogs, cats, pigs, horses, goats, sheep, rodent animals (for example, mice, rats, hamsters, guinea pigs), and rabbits. In an exemplary embodiment, the cells constituting the sheet-shaped cell culture are human cells.

The cells forming the sheet-shaped cell culture may be heterologous cells or may be homologous cells. Here, the term "heterologous cells" means cells derived from an organism of a species different from that of the recipient, in the case where the sheet-shaped cell culture is used for transplantation. For instance, in the case where the recipient is a human, cells derived from a monkey or a pig correspond to the heterologous cells. In addition, the term "homologous cells" means cells derived from an organism of the same species as that of the recipient. For example, in the case where the recipient is a human, human cells correspond to the homologous cells. The homologous cells include self-derived cells (also called self cells or autologous cells), namely, cells derived from the recipient, and homologous non-autologous cells (also called allogeneic cells). The autologous cells are preferred in the present disclosure, since they do not cause rejection when transplanted. However, heterologous cells and homologous non-autologous cells can also be utilized. In the cases where heterologous cells or homologous non-autologous cells are utilized, an immune suppression treatment may be needed, for suppressing rejection. Note that herein other cells than autologous cells, namely, heterologous cells and homologous non-autologous cells may be generically referred to as non-autologous cells. In an embodiment of the present disclosure, the cells are autologous cells or allogeneic cells. In an exemplary embodiment of the present disclosure, the cells are autologous cells. In another exemplary embodiment of the present disclosure, the cells are allogeneic cells.

The autologous or allogeneic pluripotent stem cells can be obtained by, for example, but not limited to, introducing a gene such as OCT3/4, SOX2, KLF4, or C-MYC into harvested autologous or allogeneic somatic cells (for example, skin cells (fibroblasts, keratinocytes, etc.), blood corpuscles (peripheral blood mononuclear cells)) so as thereby to derive autologous or allogeneic iPS cells. The method for deriving iPS cells from somatic cells is known in this technical field (see, for example, Bayart and Cohen-Haguenauer, Curr Gene Ther. 2013 April; 13(2): 73-92).

The sheet-shaped cell culture can be produced by any known method (see, for example, JP-A-2007-528755, Shimizu et al., Circ Res. 2002 Feb. 22; 90(3): e40-e48, Matsuura et al., Biomaterials. 2011 October; 32(30): 7355-62, and Kawamura et al., Circulation. 2012 Sep. 11; 126(11 Suppl 1): S29-37). The method of producing the sheet-shaped cell culture, can include a step of inoculating cells on a culture substrate, a step of culturing the inoculated cells to form a sheet-shaped cell culture, and a step of isolating the thus formed sheet-shaped cell culture from the culture substrate, but this is not limitative.

The culture substrate is not particularly limited so long as it permits the cells to form a cell culture thereon, and examples of the culture substrate include containers made of various materials, and solid or semi-solid surfaces in containers. The container is preferably of a structure and a material that prevent liquids such as culture liquid from permeating therethrough. Examples of such a material include, but are not limited to, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethylacrylamide, and metals (for example, iron, stainless steel, aluminum, copper, brass). In addition, the container preferably has at least one flat surface. Examples of such a container include, but are not limited to, cell culture dishes and cell culture bottles. Moreover, the container may have a solid or semi-solid surface in the inside thereof. Examples of a solid surface include plates and containers of the aforesaid various materials, and examples of a semi-solid surface include gels and flexible polymer matrixes. The culture substrate may be produced by use of the above-mentioned material, or a commercialized one may be utilized. Examples of a preferred culture substrate include, but are not limited to, substrates having an adhesive surface suitable for formation of a sheet-shaped cell culture. Specific examples of the preferred culture substrates include substrates having a hydrophilic surface, for example, substrates having a surface coated with a hydrophilic compound such as corona discharge-treated polystyrene, collagen gel or hydrophilic polymer, and, further, substrates having a surface coated with collagen, fibronectin, laminin, vitronectin, proteoglycan, glycosaminoglycan or the like extracellular matrix, or cadherin family, selectin family, integrin family or the like cell adhesion factor. In addition, such substrates are commercially available (for example, Corning (registered trademark) TC-Treated Culture Dish, made by Corning Incorporated).

The culture substrate may have its surface coated with a material of which properties change in response to a stimulus, for example, temperature or light. As such a material, the followings that are publically known, but not limited thereto, can be used: for example, temperature-responsive materials consisting of homopolymers or copolymers of (meth)acrylamide compounds, N-alkyl-substituted (meth)acrylamide derivatives (for example, N-ethylacrylamide, N-n-propylacrylamide, N-n-propylmethacrylamide, N-isopropylacrylamide, N-isopropylmethacrylamide, N-cyclopropylacrylamide, N-cyclopropylmethacrylamide, N-ethoxyethylacrylamide, N-ethoxyethylmethacrylamide, N-tetrahydrofurfurylacrylamide, N-tetrahydrofurfurylmethacrylamide, etc.), N,N-dialkyl-substituted (meth)acrylamide derivatives (for example, N,N-dimethyl(meth)acrylamide, N,N-ethylmethylacrylamide, N,N-diethylacrylamide), (meth)acrylamide derivatives having a cyclic group (for example, 1-(1-oxo-2-propenyl)-pyrrolidine, 1-(1-oxo-2-propenyl)-piperidine, 4-(1-oxo-2-propenyl)-morpholine, 1-(1-oxo-2-methyl-2-propenyl)-pyrrolidine, 1-(1-oxo-2-methyl-2-propenyl)-piperidine, 4-(1-oxo-2-methyl-2-propenyl)-morpholine, etc.), or vinyl ether derivatives (for example, methyl vinyl ether), and light-responsive materials such as light-absorptive polymers having an azobenzene group, copolymers of a vinyl derivative of triphenylmethane leucohydroxide with an acrylamide monomer, and N-isopropylacrylamide gel including spirobenzopyran, etc. (see, for example, JP-A-1990-211865, JP-A-2003-33177). By giving a predetermined stimulus to these materials, the properties of the material, for example, hydrophilicity or hydrophobicity can be changed, whereby peeling of a cell culture adhering to the material can be promoted. Culture dishes coated with a temperature-responsive material are commercially available (for example, UpCell (registered trademark), made by Cell-Seed Inc.), and they can be used in the producing method of the present disclosure.

In an exemplary embodiment, the sheet-shaped cell culture of the present disclosure is higher in cytokine producing ability than a sheet-shaped cell culture obtained by culturing a cell population wherein the proportion of the number of myocardial cells derived from pluripotent stem cells to the total number of cells in the cell population is not more than 25% or not less than 90%. The cytokine producing ability means the ability to produce cytokine, and can be evaluated based on an arbitrary index concerning cytokine production such as, for example, but being not limited to, the amount of cytokine released from the sheet-shaped cell culture, the amount of cytokine included in the sheet-shaped cell culture, and the amount of a cytokine gene expressed by the cells constituting the sheet-shaped cell culture.

In the present disclosure, the cytokine means a proteinous factor that is released from cells and intermediates various intercellular interactions. Therefore, the cytokine in the present disclosure is not limited to those released from immunocytes. In an exemplary embodiment of the present disclosure, the cytokine has an activity of promoting engraftment of the sheet-shaped cell culture onto a tissue to which the sheet-shaped cell culture is to be transplanted. In an exemplary embodiment of the present disclosure, the cytokine has angiogenic activity. In an exemplary embodiment of the present disclosure, the cytokine has an activity of promoting regeneration or repair of tissue. In an exemplary embodiment of the present disclosure, the cytokine has an activity of mobilizing stem cells (for example, cardiac stem cells, bone marrow stem cells). Such cytokines are known in this technical field, and one skilled in the art can determine a suitable cytokine, based on known information (see, for example, Lui et al., Stem Cell Res. 2014 Jul. 8. pii: S1873-5061(14)00080-4, Cochain et al., Antioxid Redox Signal. 2013 Mar. 20; 18(9): 1100-13). In an exemplary embodiment of the present disclosure, the cytokine includes growth factors. In an exemplary embodiment of the present disclosure, the cytokine has an angiogenic activity and/or a stem cell mobilizing activity. In a specific exemplary embodiment of the present disclosure, the cytokine is selected from the group consisting of VEGF and SCF. Therefore, in an exemplary embodiment of the present disclosure, the cytokine producing ability is a growth factor producing ability. Moreover, in an exemplary embodiment of the present disclosure, the cytokine producing ability is an ability to produce a cytokine that has an angiogenic activity and/or a stem cell mobilizing ability. Further, in a specific exemplary embodiment of the present disclosure, the cytokine producing ability is an ability to produce a growth factor selected from the group consisting of VEGF and SCF.

The amount of the cytokine released from the sheet-shaped cell culture can be obtained by, for example, but not limited to, a method wherein the sheet-shaped cell culture is cultured in a culture liquid for a predetermined period and thereafter the amount of cytokine (for example, the concentration of cytokine) included in the culture liquid (culture supernatant) is measured. The amount of the cytokine included in the sheet-shaped cell culture can be obtained by, for example, but not limited to, a method wherein the sheet-shaped cell culture is cultured in a culture liquid for a predetermined period, thereafter the sheet-shaped cell culture is crushed or dissolved, and the amount of cytokine (for example, the concentration of cytokine) included in the thus obtained crushed liquid or solution is measured. The amount of a cytokine gene expressed by the cells constituting the sheet-shaped cell culture can be obtained by, for example, but not limited to, a method wherein total RNA is extracted from the sheet-shaped cell culture and the amount of a cytokine gene included in the extracted RNA is determined.

The techniques for measuring the amount of a cytokine or the expression amount of a cytokine gene are known in this technical field. Examples of the technique for measuring the amount of a cytokine include, but are not limited to, an electrophoresis method, a western blotting method, mass spectrometry, EIA (for example, ELISA), RIA (for example, IRMA, RAST, RIST), magnetic immunoassay (MIA, for example, immunoassay using magnetic beads), an immunohistochemical method, and an immunocytochemical method. Examples of the technique for measuring the expression amount of a cytokine gene include, but are not limited to, a northern blotting method, a southern blotting method, DNA microarray analysis, RNase protection assay, RT-PCR, real-time PCR and the like PCR methods, and an in situ hybridization method.

The expression "higher in cytokine producing ability" means that the cytokine producing ability of the sheet-shaped cell culture of the present disclosure is higher than the cytokine producing ability of a control sheet-shaped cell culture (namely, a sheet-shaped cell culture obtained by culturing a cell population wherein the proportion of the number of myocardial cells derived from pluripotent stem cells to the total number of cells in the cell population is not more than 25% or not less than 90%) by, for example, not less than approximately 10%, not less than approximately 20%, not less than approximately 30%, not less than approximately 40%, not less than approximately 50%, not less than approximately 60%, not less than approximately 70%, not less than approximately 80%, not less than approximately 90%, not less than approximately 100%, not less than approximately 110%, not less than approximately 120%, not less than approximately 130%, not less than approximately 140%, not less than approximately 150%, not less than approximately 160%, not less than approximately 170%, not less than approximately 180%, not less than approximately 190%, not less than approximately 200%, not less than approximately 250%, not less than approximately 300%, not less than approximately 350%, not less than approximately 400%, not less than approximately 450%, not less than approximately 500%, not less than approximately 550%, not less than approximately 600%, or not less than approximately 650%.

In an exemplary embodiment, the sheet-shaped cell culture of the present disclosure is substantially germfree. In an exemplary embodiment, the sheet-shaped cell culture of the present disclosure is germfree.

Another aspect of the present disclosure relates to a method of producing the above-mentioned sheet-shaped cell culture, the method including:

(1) a step of subjecting pluripotent stem cells to a myocardial cell derivation treatment to obtain a first cell population including myocardial cells;

(2) a step of obtaining a second cell population including the myocardial cells derived from the first cell population obtained in the step (1); and (3) a step of culturing the second cell population obtained in the step (2) to form a sheet-shaped cell culture, wherein the proportion of the number of the myocardial cells to the total number of cells in the second cell population is more than approximately 25% and less than approximately 90%, preferably approximately 30% to approximately 80%, more preferably approximately 40% to approximately 75%, and particularly preferably approximately 50% to approximately 70% (the method may hereinafter be referred to as "the producing method of the present disclosure").

The myocardial cell derivation treatment of pluripotent stem cells, the isolation of myocardial cells from a cell population, the sheet-shaped cell culture, and the formation of the sheet-shaped cell culture are as described above in regard of the sheet-shaped cell culture of the present disclosure. In carrying out the step (2), the myocardial cells may be purified from the first cell population to enhance the purity of the myocardial cells and thereby to obtain the second cell population, or part of the myocardial cells may be removed from the first cell population to lower the purity of the myocardial cells and thereby to obtain the second cell population, or a myocardial cell population purified from the first cell population may be mixed with other cell population to thereby obtain the second cell population. In an exemplary embodiment, the second cell population is obtained by mixing a myocardial cell population obtained by purification of the first cell population with non-myocardial cells in such a manner that the proportion of the number of the myocardial cells to the total number of cells in the second cell population becomes more than approximately 25% and less than approximately 90%, preferably approximately 30% to approximately 80%, more preferably approximately 40% to approximately 75%, and particularly preferably approximately 50% to approximately 70%.

The second cell population may include one or more kinds of non-myocardial cells selected from the group consisting of αSMA positive cells, CD31 positive cells, and TE-7 antigen positive cells, and, preferably, may include all the three kinds of cells of the αSMA positive cells, CD31 positive cells, and TE-7 antigen positive cells. The αSMA positive cells, CD31 positive cells, and TE-7 antigen positive cells and the method for obtaining these cells are as described above in regard of the sheet-shaped cell culture of the present disclosure. In addition, the proportions of the number of αSMA positive cells, the number of CD31 positive cells, and the number of TE-7 antigen positive cells to the total number of cells in the second cell population are as described above in regard of "the cell population including the myocardial cells derived from pluripotent stem cells" of the sheet-shaped cell culture of the present disclosure.

In a specific exemplary embodiment, the step (2) includes mixing a myocardial cell population obtained by purification of the first cell population with a non-myocardial cells obtained after removal of the myocardial cells from the first cell population in a predetermined proportion, for example, in such a manner that (the number of myocardial cells):(the number of non-myocardial cells) becomes (more than approximately 25 and less than approximately 90):(more than approximately 10 and less than approximately 75), preferably (approximately 30 to approximately 80):(approximately 20 to approximately 70), more preferably (approximately 40 to approximately 75):(approximately 25 to approximately 60), and particularly preferably (approximately 50 to approximately 70):(approximately 30 to approximately 50).

The producing method of the present disclosure may further include, after the step of forming the sheet-shaped cell culture, a step of recovering the sheet-shaped cell culture formed. The recovery of the sheet-shaped cell culture is not particularly limited so long as the sheet-shaped cell culture can be detached (peeled) from a culture substrate serving as a scaffold, while at least partly maintaining a sheet structure; for instance, the removal can be performed by an enzymatic treatment by a protease (for example, trypsin) and/or a mechanical treatment such as pipetting. In addition, in the case where the sheet-shaped cell culture is formed by culturing cells on a culture substrate having a surface coated with a material of which properties change in response to a stimulus, for example, temperature or light, the sheet-shaped cell culture can also be non-enzymatically detached by exerting a predetermined stimulus. For example, in the case where the cell culture is formed by culturing cells on a temperature-responsive culture dish, the sheet-shaped cell culture can be non-enzymatically detached by setting the temperature to be not higher than a lower critical solution temperature (LCST) or not lower than an upper critical solution temperature (UCST) of the temperature-responsive material with respect to water.

In an exemplary embodiment, all the steps in the producing method of the present disclosure are carried out in vitro. In another exemplary embodiment, the producing method of the present disclosure can include a step carried out in vivo, examples of which include, but are not limited to, a step of harvesting cells (for example, skin cells, blood corpuscles, etc. in the case of using iPS cells) or tissue serving as a supply source of the cells (for example, skin tissue, blood, etc. in the case of using iPS cells) from a subject. In an exemplary embodiment, all the steps in the producing method of the present disclosure are carried out under a germfree condition. In an exemplary embodiment, the producing method of the present disclosure is performed in such a manner that the sheet-shaped cell culture obtained finally becomes substantially germfree. In an exemplary embodiment, the producing method of the present disclosure is conducted in such a manner that the sheet-shaped cell culture obtained finally becomes germfree.

Another aspect of the present disclosure relates to a composition, graft, medical product and the like including the sheet-shaped cell culture of the present disclosure (they may hereinafter be generically referred to as "composition, etc.").

The composition, etc. of the present disclosure may include, in addition to the sheet-shaped cell culture of the present disclosure, various additional components, for example, a pharmaceutically permissible carrier, components for enhancing the viability, engraftment properties and/or functions of the sheet-shaped cell culture, other effective components useful for treatment of a target disease, etc. As such additional components, any of those known can be used, and those skilled in the art are well familiar with these additional components. Moreover, the composition, etc. of the present disclosure can be used jointly with components for enhancing the viability, engraftment properties and/or functions of the sheet-shaped cell culture, other effective components useful for treatment of a target disease, etc.

In an exemplary embodiment, the sheet-shaped cell culture and the composition, etc. of the present disclosure are for treatment of a disease (for example, heart disease). In addition, the sheet-shaped cell culture of the present disclosure can be used for production of a composition, etc. for treatment of a disease (for example, heart disease). Examples of the disease include, but are not limited to, myocardial infarction (inclusive of chronic cardiac insufficiency accompanying myocardial infarction), dilated cardiomyopathy, ischemic cardiomyopathy, and heart diseases accompanied by systolic functional disorder (for example, left ventricular systolic functional disorder) (for example, cardiac insufficiency, particularly chronic cardiac insufficiency). The cytokine (for example, VEGF, SCF) produced by the sheet-shaped cell culture of the present disclosure can contribute to treatment of a disease. The disease may be one for treatment of which the cytokine selected from the group consisting of VEGF and SCF, myocardial cells, and/or the sheet-shaped cell culture (cell sheet) is useful.

Another aspect of the present disclosure relates to a kit for producing the sheet-shaped cell culture or the composition, etc. of the present disclosure, and/or for treating a disease by use of the sheet-shaped cell culture or the composition, etc. of the present disclosure, including part or all of elements used for production of the sheet-shaped cell culture or the composition, etc. of the present disclosure (such a kit may hereinafter be referred to as "the kit of the present disclosure"). The kit of the present disclosure may include, for example, but not limited to, cells for use in culture of the sheet-shaped cell culture (for example, pluripotent stem cells, a cell population obtained by subjecting pluripotent stem cells to a myocardial cell derivation treatment (a first cell population), myocardial cells isolated from the first cell population, a non-myocardial cell population obtained by removal of a myocardial cell population from the first cell population, a cell population including myocardial cells (and, optionally, predetermined non-myocardial cells) derived from pluripotent stem cells in a predetermined proportion (a second cell population), etc.), culture liquid, culture dishes, reagents for use in purification of myocardial cells (for example, antibodies, cleaning liquid, beads, etc.), implements (for example, pipette, dropping pipette, tweezers, etc.), instructions concerning the producing method and the using method for the sheet-shaped cell culture (for example, medium, such as flexible disc, compact disc (CD), digital versatile disc (DVD), Blu-ray disc, memory card, universal serial bus (USB) memory, etc. on which a manual or information concerning the producing method and the using method is recorded).

Another aspect of the present disclosure relates to a method of treating a disease in a subject, including applying an effective amount of the sheet-shaped cell culture or the composition of the present disclosure to a subject in need thereof. The target disease to be treated is as described above in regard of the sheet-shaped cell culture and the composition of the present disclosure.

In the present disclosure, the term "subject" means any living individual, preferably an animal individual, more preferably a mammal individual, still more preferably a human individual. In the present disclosure, the subject may be healthy, or may be suffering from some disease. In the case where a treatment of a disease associated with an abnormality of tissue is intended, the subject means a subject suffering from the disease or a subject having a risk of suffering from the disease.

In addition, the term "treatment" include all kinds of medically permissible prophylactic and/or therapeutic interventions for the purpose of curing, temporary remission or prevention of a disease. For instance, the term "treatment" includes medically permissible interventions for various purposes, inclusive of delaying or stopping of the progress of a disease associated with an abnormality of tissue, involution or disappearance of a lesion, prophylaxis of crisis of the disease or prevention of recurrence of the disease.

In the treating method of the present disclosure, components for enhancing the viability, engraftment properties and/or functions of the sheet-shaped cell culture, other effective components useful for treatment of a target disease, can be used jointly with the sheet-shaped cell culture or the composition of the present disclosure. Moreover, in the treating method of the present disclosure, a cytokine (for example, VEGF, SCF) produced by the sheet-shaped cell culture of the present disclosure can contribute to the treatment of a disease.

The treating method of the present disclosure may further include a step of producing the sheet-shaped cell culture of the present disclosure, in accordance with the producing method of the present disclosure. The treating method of the present disclosure may further include, before the step of producing the sheet-shaped cell culture, a step of harvesting cells for producing a sheet-shaped cell culture (for example, skin cells or blood corpuscles, in the case of using iPS cells) or a tissue serving as a supply source of the cells (for example, skin tissue or blood, in the case of using iPS cells) from a subject. In an exemplary embodiment, the subject from which the cells or the tissue serving as a supply source of the cells is harvested is the same individual as the subject to which the sheet-shaped cell culture or the composition, etc. is to be administered. In another exemplary embodiment, the subject from which the cells or the tissue serving as a supply source of the cells is harvested is a different individual of the same kind as that of the subject to which the sheet-shaped cell culture or the composition is to be administered. In another exemplary embodiment, the subject from which the cells or the tissue serving as a supply source of the cells is harvested is an individual of a different species from that of the subject to which the sheet-shaped cell culture or the composition is to be administered.

In the present disclosure, the effective amount is, for example, an amount (for example, size, weight, number of sheets, or the like of the sheet-shaped cell culture) that can suppress the crisis or recurrence of a disease, mitigate the symptom of a disease, or delay or stop the progress of a disease, and is preferably an amount that prevents the crisis or recurrence of the disease or cures the disease. In addition, the effective amount is preferably an amount such that a bad influence in excess of the advantage obtained by the administration is not generated. Such an amount can be appropriately determined by, for example, tests using experimental animals such as mice, rats, dogs or pigs or disease model animals, and the methods of such tests are well known to those skilled in the art. Moreover, the size of tissue lesion to be subjected to a treatment can be an important index for determination of the effective amount.

Examples of the method of administration include direct application to tissue. While the frequency of administration can be once per treatment, multiple-time administration can be adopted in the case where a desired effect cannot be obtained by one-time administration. In application to tissue, the sheet-shaped cell culture or the composition of the present disclosure may be fixed to the target tissue by locking means such as suture or staple.

Another aspect of the present disclosure relates to a method of enhancing cytokine producing ability of a sheet-shaped cell culture including myocardial cells derived from pluripotent stem cells, the method including:

(1) a step of subjecting pluripotent stem cells to a myocardial cell derivation treatment to obtain a first cell population including myocardial cells;

(2) a step of obtaining a second cell population including the myocardial cells derived from the first cell population obtained in the step (1); and (3) a step of culturing the second cell population obtained in the step (2) to form a sheet-shaped cell culture, wherein the proportion of the number of the myocardial cells to the total number of cells in the second cell population is more than approximately 25% and less than approximately 90%, preferably approximately 30% to approximately 80%, more preferably approximately 40% to approximately 75%, and particularly preferably approximately 50% to approximately 70% (the method may hereinafter be referred to as "the cytokine producing ability enhancing method").

Each of the steps in the cytokine producing ability enhancing method of the present disclosure is as described above in regard of the producing method of the present disclosure. In addition, the expression "to enhance the cytokine producing ability" means to enhance the cytokine producing ability of the sheet-shaped cell culture as compared to the cytokine producing ability of a control sheet-shaped cell culture (namely, a sheet-shaped cell culture obtained by culturing a cell population wherein the proportion of the number of myocardial cells derived from pluripotent stem cells to the total number of cells in the cell population is not more than 25% or not less than 90%) by a factor of, for example, not less than approximately 10%, not less than approximately 20%, not less than approximately 30%, not less than approximately 40%, not less than approximately 50%, not less than approximately 60%, not less than approximately 70%, not less than approximately 80%, not less than approximately 90%, not less than approximately 100%, not less than approximately 110%, not less than approximately 120%, not less than approximately 130%, not less than approximately 140%, not less than approximately 150%, not less than approximately 160%, not less than approximately 170%, not less than approximately 180%, not less than approximately 190%, not less than approximately 200%, not less than approximately 250%, not less than approximately 300%, not less than approximately 350%, not less than approximately 400%, not less than approximately 450%, not less than approximately 500%, not less than approximately 550%, not less than approximately 600%, or not less than approximately 650%.

The present disclosure is described more in detail, referring to the following examples, but these are specific examples of the present disclosure and are not to be limitative of the disclosure.

Example 1: Derivation of Myocardial Cells from Human iPS Cells

Human iPS cells (253G1 strain) were purchased from Riken BioResource Center, and were maintained on mouse embryo fibroblasts (MEF, made by RiproCELL Inc.) subjected to a mitomycin C treatment, in a Primate ES Cell Medium (made by RiproCELL Inc.) to which 5 ng/mL of basic fibroblast growth factor (bFGF, made by RiproCELL Inc., here and hereinafter) had been added, in a culture dish having a diameter of 10 cm. Subculture of the cells was conducted every three to four days by use of a cell peeling liquid (CTK solution, made by RiproCELL Inc., here and hereinafter) while maintaining a colony (without conversion into a single cell suspension).

Deviation to myocardial cells was conducted by making predetermined additives act on embryoid body (EB) in suspension culture at predetermined timings. Human iPS cell aggregates (approximately $2 \times 10^7$ cells) peeled from ten culture dishes by the cell peeling liquid were re-suspended in 100 mL of mTeSR (trademark) 1 (made by STEMCELL Technologies Inc.) to which 10 µM of a ROCK inhibitor (Y-27632, made by Wako Pure Chemical Industries, Ltd.) had been added, and were introduced into a culture apparatus provided with stirrer (Bio Jr. 8, made by Able Corporation). During the culture, the stirring rate was kept at 40 rpm, the dissolved oxygen concentration was kept at 40%, pH was kept at 7.2, and temperature was kept at 37° C. Control of the dissolved oxygen concentration was conducted by use of air, oxygen, or nitrogen, and control of pH was performed by addition of $CO_2$.

After one day (on first day) of the start of culture (zeroth day) in a culture apparatus, the medium was replaced with a basal medium for myocardial cell derivation (StemPro (registered trademark)-34 SFM (made by Life Technologies Corporation) including 50 μg/mL of ascorbic acid (made by Sigma-Aldrich Corporation), 2 mM of L-glutamine and 400 μM of 1-thioglycerol (made by Sigma-Aldrich Corporation)) to which 0.5 ng/mL of BMP4 (made by R&D Systems Inc., here and hereinafter) had been added. Thereafter, the medium was replaced with the basal media for myocardial cell derivation including the following additives at the following timings. Second day: 10 ng/mL of BMP4, 5 ng/mL of bFGF, and 3 ng/mL of activin A (made by R&D Systems, Inc.), fifth day: 4 μM of a Wnt signal inhibitor (IWR-1-endo, made by Wako Pure Chemical Industries, Ltd.), seventh day: 5 ng/mL of VEGF (made by R&D Systems, Inc.) and 10 ng/mL of bFGF. Thereafter, medium replacement was conducted on ninth, 11th, 13th and 15th days by use of the same medium as used on seventh day (namely, the basal medium for myocardial cell derivation to which 5 ng/mL of VEGF and 10 ng/mL of bFGF had been added). In this manner, a cell population (cell mass) including myocardial cells derived from human iPS cells was obtained. The cell population was dissociated by 0.05% trypsin/EDTA, after which the remaining cell aggregates were removed by use of a strainer (made by BD Bioscience), and the cell population was put to the subsequent experiments.

Example 2: Analysis of Composition Ratio of Non-Myocardial Cells

Using part of the dissociated cell population obtained in Example 1, the composition ratio of non-myocardial cells in the cell population was examined. First, the cell population was subjected to double labeling with respect to both a non-myocardial cell marker (CD31 which is a marker of vascular endothelial cells, etc., αSMA which is a marker of smooth muscle cells, etc., or TE-7 antigen which is a marker of fibroblasts, etc.) and c-TNT which is a myocardial cell marker.

Labeling of the CD31 expressing cells was carried out by reacting the cell population with PE binding anti-human CD31 antibody (clone WM59, mouse IgG1, made by Becton, Dickinson and Company), thereafter subjecting the cells to a fixation/permeation treatment using a fixation/permeation treating agent (BD Cytofix/Cytoperm (trademark) Fixation/Permeabilization Solution Kit, made by Becton, Dickinson and Company), and reacting the thus treated cells with anti-c-TNT antibody (Troponin T-C Antibody (CT3), mouse IgG2a, made by Santa Cruz Biotechnology, Inc., here and hereinafter) and then with fluorescence-labeled secondary antibody (Alexa Fluor (registered trademark) 647 binding anti-mouse IgG2a antibody, made by Life Technologies Corporation).

Labeling of the αSMA expressing cells was carried out by subjecting the cells to a fixation/permeation treatment using a fixation/permeation treating agent, and reacting the thus treated cells with anti-c-TNT antibody and anti-αSMA antibody (clone E184, rabbit IgG, made by Abcam plc), and then with fluorescence-labeled secondary antibodies (Alexa Fluor (registered trademark) 647 binding anti-mouse IgG2a antibody and Alexa Fluor (registered trademark) 488 binding anti-rabbit antibody, both made by Life Technologies Corporation) that bind to the above-mentioned primary antibodies.

Labeling of the TE-7 antigen expressing cells was carried out by subjecting the cells to a fixation/permeation treatment using a fixation/permeation treating agent, and reacting the thus treated cells with anti-c-TNT antibody and anti-human fibroblast antibody (clone TE-7, mouse IgG1, made by Merck Millipore Corporation), and then with fluorescence-labeled secondary antibodies (Alexa Fluor (registered trademark) 647 binding anti-mouse IgG2a antibody and Alexa Fluor (registered trademark) 488 binding anti-mouse IgG1 antibody, both made by Life Technologies Corporation) that bind to the above-mentioned primary antibodies.

The labeled cells were analyzed by use of BD FACSCanto (trademark) II flow cytometer and BD FACSDiva (trademark) software (both made by Becton, Dickinson and Company). The proportions of the numbers of non-myocardial cell marker positive cells to the total number of cells in the non-myocardial cell population were calculated as the proportions of the numbers of non-myocardial cell marker positive cells to the total number of cells in the cell population (non-myocardial cell population) of the c-TNT negative fraction. The results are set forth in Table 1 below.

TABLE 1

| Proportions of each non-myocardial cell marker positive cells in non-myocardial cell population | | | |
|---|---|---|---|
| | CD31 (%) | TE-7 antigen (%) | αSMA (%) |
| Experiment 1 | 5.4 | 0.65 | 88.2 |
| Experiment 2 | 4.0 | 31.1 | 86.1 |
| Average | 4.7 | 15.9 | 87.2 |

Example 3: Separation of Myocardial Cells

Part of the dissociated cell population obtained in Example 1 was labeled with PE (phycoerythrin) binding anti-human CD172a/b antibody (clone SE5A5, made by BioLegend, Inc.) that specifically binds to CD172 which is a myocardial cell marker. The labeled cells were loaded with anti-PE microbeads (made by Miltenyi Biotec GmbH), and a mixture of the cells and the beads was passed through LS Columns (made by Miltenyi Biotec GmbH) disposed on MidiMACS (trademark) Separator (made by Miltenyi Biotec GmbH), to separate the cells into a myocardial cell population including myocardial cells positive for CD172 and a non-myocardial cell population including non-myocardial cells negative for CD172.

Using part of the separated myocardial cell population, the proportion of the number of cells that express c-TNT which is another myocardial cell marker to the total number of cells in the separated myocardial cell population was analyzed by flow cytometry. Specifically, the separated myocardial cell population was subjected to a fixation/permeation treatment using a fixation/permeation treating agent, the thus treated cells were reacted with anti-c-TNT antibody and then with a fluorescence-labeled secondary antibody (Alexa Fluor (registered trademark) 647 binding anti-mouse IgG2a antibody, made by Life Technologies Corporation), and thereafter the labeled cells were analyzed by use of BD FACSCanto (trademark) II flow cytometer and BD FACSDiva (trademark) software (both made by Becton, Dickinson and Company). As a result of the analysis, it was found that the proportion of the number of c-TNT positive cells to the total number of cells in the myocardial cell population separated above was more than 90%.

Example 4: Production of Sheet-Shaped Cell Culture

The myocardial cell population and the non-myocardial cell population separated in Example 3 were mixed in the ratios set forth in Table 2 below, to prepare cell populations A to D for forming sheet-shaped cell cultures.

TABLE 2

Constitution of cell populations A to D

|  | Proportion of myocardial cell population (%) | Proportion of non-myocardial cell population (%) |
|---|---|---|
| Cell population A | 25 | 75 |
| Cell population B | 50 | 50 |
| Cell population C | 70 | 30 |
| Cell population D | 90 | 10 |

Note that the proportion (%) in the table means the proportion of the number of cells in cell populations of various kinds to the total number of cells in the cell population. In addition, the proportions of the non-myocardial cell marker positive cells in the non-myocardial cell population calculated in Example 2 are considered to be substantially unchanged across the separating step, and, therefore, can be applied also to the non-myocardial cell population after the separation.

Figure 1:
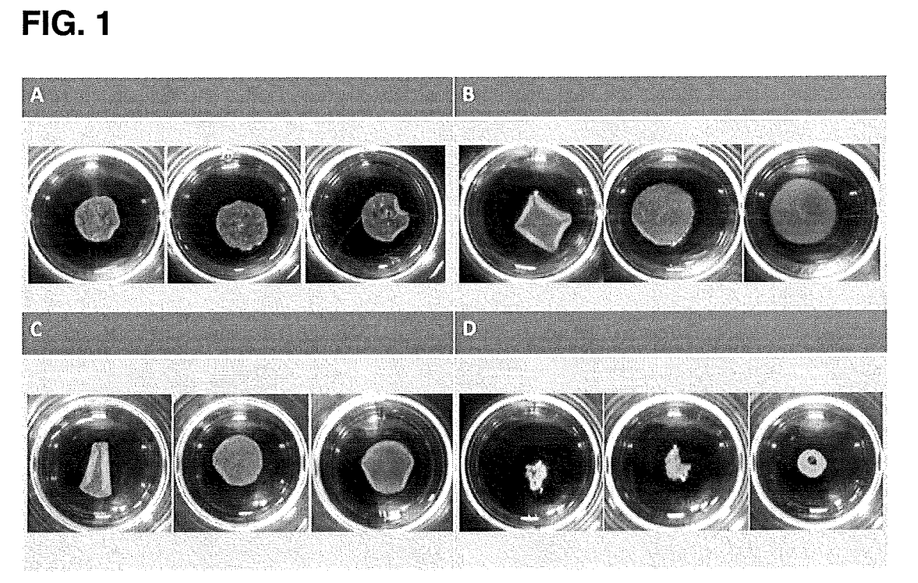
FIG. 1 depicts photographs of external appearances of completed sheet-shaped cell cultures A to D.

The cell populations A to D were each inoculated on temperature-responsive culture dishes (UpCell (registered trademark), made by CellSeed Inc.) in a density of $2.1 \times 10^5$ cells/cm$^2$, then were grown and cultured in 10% FBS-added DMEM not including a ROCK inhibitor at 37° C. and 5% $CO_2$ for five days to form sheet-shaped cell cultures, and the sheet-shaped cell cultures were peeled from the culture dishes by a temperature treatment (leaving to stand still at room temperature for approximately 10 to 30 minutes) (FIG. 1). Hereinafter, the sheet-shaped cell cultures formed from the cell populations A to D are described as sheet-shaped cell cultures A to D, respectively, and shown in FIG. 1.

Example 5: Evaluation of Sheet-Shaped Cell Culture (1) External Appearance

The sheet-shaped cell cultures B to D formed from the cell populations wherein the proportions of the myocardial cell population were not less than 50% showed voluntary synchronous beating. In addition, the sheet-shaped cell cultures A to C were able to form a white-colored circular shape suitable for transplantation, but the sheet-shaped cell culture D was unable to form a stable sheet-shaped structure (2) Production of Cytokine The sheet-shaped cell cultures A to D were cultured in a 10% FBS-added DMEM at 37° C. and 5% $CO_2$ for two days, and the concentrations of VEGF and SCF included in the culture supernatants obtained were measured using Bio-Plex (registered trademark) Suspension Array System (made by Bio-Rad Laboratories, Inc.) in accordance with the product manual (n=4). The determination of VEGF was conducted using Bio-Plex Pro (trademark) human cytokine 28-Plex assay, and the determination of SCF was performed using Bio-Plex Pro (trademark) human cytokine 21-Plex assay. Statistically significant differences between the groups were evaluated using Non-repeated Measures ANOVA.

Figure 2:
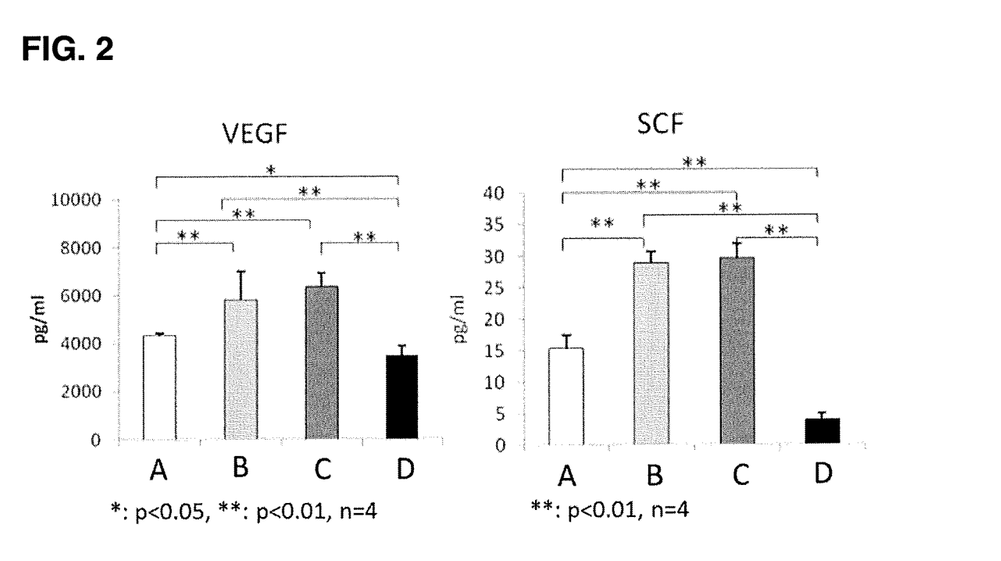
FIG. 2 is a graph depicting determination results of cytokines produced by the sheet-shaped cell cultures A to D. Note that the axis of ordinates represents the concentration of each cytokine in the culture supernatant, * indicates $p<0.05$, and ** indicates $p<0.01$.

The results depicted in FIG. 2 shows that a high cytokine production amount can be obtained when the proportion of a myocardial cell population in a cell population forming the sheet-shaped cell culture is set to be 50% to 70%. It is known that VEGF has an angiogenic activity, enhances the survival rate of grafts, and so on (for example, Suzuki et al., Circulation. 2001 Sep. 18; 104 (12 Suppl 1): I207-12), and it is known that SCF can mobilize bone marrow stem cells capable of differentiating into myocardial cells, and so on (for example, Lutz et al., Cardiovasc Res. 2008 January; 77(1): 143-50). Therefore, the sheet-shaped cell cultures of the present disclosure that have high production amounts of these cytokines are expected to have a high therapeutic effect.

(3) Expression of Extracellular Matrix Constituents

After the sheet-shaped cell cultures A to D were washed twice with PBS, total RNA was extracted by RNeasy (registered trademark) Mini (made by Qiagen N.V.). Based on the total RNA thus obtained, cDNA was synthesized using SuperScript (registered trademark) VILO (trademark) cDNA Synthesis Kit (made by Life Technologies Corporation), after which expression amounts of extracellular matrix constituents were determined by real-time PCR using TaqMan (registered trademark) Gene Expression Assays and TaqMan (registered trademark) Fast Advanced Master Mix (both made by Life Technologies Corporation). Note that Assay IDs and detected genes in TaqMan (registered trademark) Gene Expression Assays are as depicted in Table 3 below.

TABLE 3

Assay IDs and detected genes

| Assay ID | Detected gene |
|---|---|
| Hs01124081_m1 | Laminin, $\alpha 2$ |
| Hs00935293_m1 | Laminin, $\alpha 4$ |
| Hs00164004_m1 | Type I collagen, $\alpha 1$ |
| Hs00943809_m1 | Type III collagen, $\alpha 1$ |

Type I and Type III collagens were expressed more in the sheet-shaped cell cultures A and B; on the other hand, laminins $\alpha 2$ and $\alpha 4$ which are main constituents of the extracellular matrix of the cardiac tissue were expressed more in the sheet-shaped cell culture C.

(4) Electric Conduction Rate

For the sheet-shaped cell cultures A to D, electric conduction rate was measured by a multi-electrode array. The cell populations A to D prepared in Example 4 were each inoculated on MED probes (made by Alpha MED Scientific, Inc.) in a density of $2.1 \times 10^5$ cells/cm$^2$. After growing culture was conducted in a 10% FBS-added DMEM at 37° C. and 5% $CO_2$ for five days to form sheet-shaped cell cultures, extracellular potential was measured using a MED64 system (made by Alpha MED Scientific, Inc.) while keeping the sheet-shaped cell cultures adhered to probes, peak time of each channel was detected using MED64 Mobius (made by WitWerx, Inc.), and conduction rate was calculated. The conduction rates of the sheet-shaped cell cultures B, C, and D were respectively 3.5±1.8 cm/second, 8.6±2.8 cm/second, and 16±5.0 cm/second; thus, the conduction rate became higher as the proportion of the myocardial cell population became higher.

The various characteristic features of the present disclosure described herein can be combined variously, and embodiments obtained by such combinations, inclusive of those not specifically described herein, are all within the scope of the present disclosure. In addition, those skilled in the art understand that a multiplicity of various modifications are possible without departing from the spirit of the present disclosure, and the equivalents including such modifications are within the scope of the present disclosure. Therefore, the embodiments described herein are merely exemplification, and it is to be understood that these embodiments are not described with an intention to restrict the scope of the present disclosure.

The detailed description above describes a sheet-shaped cell culture including myocardial cells derived from pluripotent stem cells, a method of producing the same, a composition, including the sheet-shaped cell culture, and a method of treating a disease using the sheet-shaped cell culture. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method of producing a sheet-shaped cell culture, the method comprising:
   (1) a step of subjecting pluripotent stem cells to a myocardial cell derivation treatment to obtain a cell population including myocardial cells;
   (2) a step of obtaining a cell population including the myocardial cells derived from the cell population obtained in the step (1) by:
      (a) mixing the myocardial cells derived from the cell population obtained in the step (1) with non-myocardial cells, and then
      (b) removing a portion of the myocardial cells to lower purity of the myocardial cells;
      wherein the obtained cell population is 50% to 70% myocardial cells; and
   (3) a step of culturing the cell population obtained in the step (2) in the absence of a ROCK inhibitor for five days to form the sheet-shaped cell culture.

2. The method according to claim 1, wherein the sheet-shaped cell culture is higher in cytokine producing ability than a comparative sheet-shaped cell culture obtained by culturing a comparative cell population including myocardial cells derived from pluripotent stem cells to form the comparative sheet-shaped cell culture, wherein the ratio of the myocardial cells derived from pluripotent stem cells to the total number of cells in the comparative cell population is not more than 25% or not less than 90%.

3. The method according to claim 1, comprising:
   applying an amount of the sheet-shaped cell culture to a subject to treat a heart disease.

4. The method according to claim 1, wherein the step (2) obtaining the cell population including the myocardial cells derived from the cell population obtained in the step (1) further comprises, prior to step (a) mixing:
   purifying the myocardial cells obtained in the step (1) to enhance a purity of the myocardial cells.

* * * * *